(12) United States Patent
Donsbach et al.

(10) Patent No.: US 6,737,432 B2
(45) Date of Patent: May 18, 2004

(54) CRYSTALLINE FORM OF TELMISARTAN SODIUM

(75) Inventors: Kai Donsbach, Hargesheim (DE); Irmgard Hof, Ingelheim am Rhein (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/283,440

(22) Filed: Oct. 30, 2002

(65) Prior Publication Data

US 2003/0130331 A1 Jul. 10, 2003

Related U.S. Application Data

(60) Provisional application No. 60/351,443, filed on Jan. 24, 2002.

(30) Foreign Application Priority Data

Oct. 31, 2001 (DE) .......................................... 101 53 737

(51) Int. Cl.[7] ................... A61K 31/4184; C07D 403/04

(52) U.S. Cl. ..................................... 514/394; 548/305.4
(58) Field of Search ........................ 548/305.4; 514/394

(56) References Cited

U.S. PATENT DOCUMENTS

| 5,594,003 A | 1/1997 | Hauel et al. |
| 6,358,986 B1 | 3/2002 | Schneider |

FOREIGN PATENT DOCUMENTS

| CA | 2060624 | * | 8/1992 |
| EP | 0 502 314 B1 | | 5/1998 |
| WO | WO 00/43370 A1 | | 7/2000 |

* cited by examiner

*Primary Examiner*—Laura L. Stockton
(74) *Attorney, Agent, or Firm*—Robert P. Raymond; Susan K. Pocchiari; Mary-Ellen M. Devlin

(57) ABSTRACT

The invention relates to a crystalline sodium salt of 4'-[2-n-propyl-4-methyl-6-(1-methylbenzimidazol-2-yl) benzimidazol-1-ylmethyl]biphenyl-2-carboxylic acid (INN: telmisartan), processes for preparing it and the use thereof for preparing a pharmaceutical composition.

9 Claims, 1 Drawing Sheet

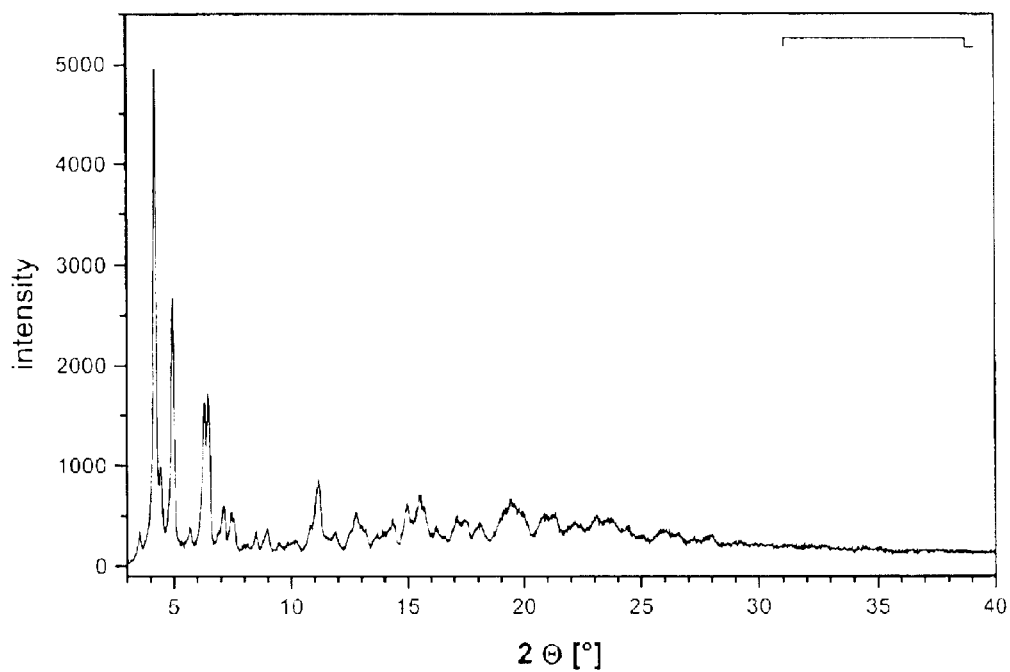
Figure 1: X-ray powder diagram of telmisartan-sodium salt

CRYSTALLINE FORM OF TELMISARTAN SODIUM

RELATED APPLICATIONS

Benefit of U.S. Provisional Application Serial No. 60/351,443, filed on Jan. 24, 2002 is hereby claimed.

FIELD OF THE INVENTION

The invention relates to a crystalline form of the sodium salt of telmisartan, processes for preparing it and the use thereof for preparing a pharmaceutical composition.

BACKGROUND OF THE INVENTION

Telmisartan is the nonproprietary name (NN, USAN and BAN) for 4'-[2-n-propyl-4-methyl-6-(1-methylbenzimidazol-2-yl)benzimidazol-1-ylmethyl]biphenyl-2-carboxylic acid. It has the following chemical structure

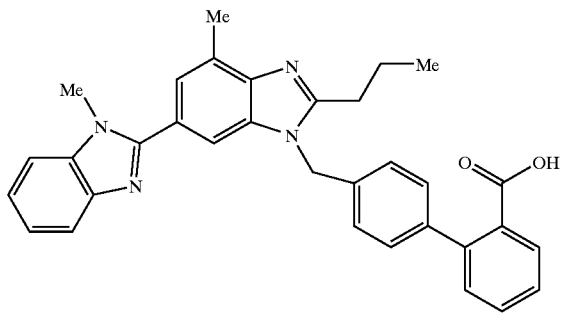

and is known from European Patent EP 502 314 B1 and U.S. Pat. No. 5,591,762.

Telmisartan, and the physiologically acceptable salts thereof, have valuable pharmacological properties. Telmisartan is an angiotensin antagonist, particularly an angiotensin-II-antagonist which by virtue of its pharmacological properties may be used for example to treat hypertension and cardiac insufficiency, to treat ischaemic peripheral circulatory disorders, myocardial ischaemia (angina), to prevent the progression of cardiac insufficiency after myocardial infarct, to treat diabetic neuropathy, glaucoma, gastrointestinal diseases and bladder diseases. Other possible therapeutic applications can be found in EP 502314 B1 and U.S. Pat. No. 5,591,762.

A pharmaceutical formulation comprising telmisartan as the active ingredient, Micardis® (telmisartan) Tablets, is commercially available. Starting from the free acid of telmisartan, the preparation in the form in which telmisartan is marketed is produced by a complex spray drying process. Because of the limited solubility of the free acid, less complex methods of preparing an alternative preparation are difficult to achieve.

Thus, one objective of the present invention is to find a less complex and easier means for preparing a crystalline form of telmisartan that would be suitable for use in the preparation of pharmaceutical formulations.

It has to be borne in mind that generally the production of a composition containing a pharmaceutically active substance is based on various parameters which are linked to the nature of the active ingredient itself. Without being tied thereto, examples of these parameters are the stability of effect of the starting material under different environmental conditions, the stability during the manufacture of the pharmaceutical formulation and the stability in the final compositions of the pharmaceutical preparation. The pharmaceutically active substance used to prepare the abovementioned pharmaceutical compositions should be as pure as possible and its stability on long-term storage must be guaranteed under various environmental conditions. This is absolutely essential, in order to prevent pharmaceutical compositions being used which contain, in addition to the active substance proper, breakdown products thereof. In such a case the content of active substance present in a preparation produced therefrom may be less than the specified amount.

Another aspect which is important in the production of solid preparations is that the active substance should have the most stable possible crystalline morphology for pharmaceutical quality. If this is not the case, the morphology of the active substance may change in certain circumstances under the conditions of manufacture of the preparation. Such a change may in turn affect the reproducibility of the manufacturing process and thus lead to final formulations which do not meet the high quality requirements imposed on formulations of pharmaceutical compositions. To this extent it should be generally borne in mind that any change to the solid state of a pharmaceutical composition which can improve its physical and chemical stability gives a significant advantage of less stable forms of the same drug.

Thus, a further object of the invention is to provide a new, stable, crystalline form of telmisartan which complies with the abovementioned stringent requirements imposed on pharmaceutically active substances.

DETAILED DESCRIPTION OF THE INVENTION

Surprisingly, it has been found that telmisartan can be obtained in crystalline form, as the sodium salt of the below formula 1.

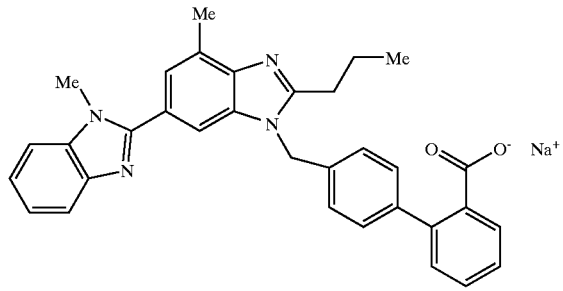

1

In accordance with conventions respecting the use of nonproprietary names, the telmisartan salt of formula 1 may be referred to as telmisartan sodium. Therefore, as used herein, the term "telmisartan sodium" is defined to mean the telmisartan salt of formula 1.

By a suitable choice of manufacturing conditions, the polymorphic form of the crystalline sodium salt which meets the requirements mentioned above can be obtained selectively.

This crystalline form of the sodium salt of telmisartan is characterised by having a melting point of $T=245\pm5°$ C. (determined by DSC=Differential Scanning Calorimetry; heating rate: 10 K/min).

The present invention therefore relates to a crystalline form of telmisartan sodium that is characterised by having a melting point of $T=245\pm5°$ C. (determined by DSC). The above value was obtained using a DSC821 made by Messrs Mettler-Toledo.

BRIEF DESCRIPTION OF THE DRAWING

The crystalline form of telmisartan sodium according to the invention was examined more closely by x-ray powder diffraction. The X-ray powder diagram obtained is shown in FIG. 1.

The following Table 1 summarizes the data obtained in this x-ray powder diffraction analysis:

TABLE 1

| 2 Θ [°] | d [Å] | rel. intensity [%] | 2 Θ [°] | d [Å] | rel. intensity [%] |
|---|---|---|---|---|---|
| 3.54 | 24.96 | 7 | 13.17 | 6.72 | 7 |
| 4.21 | 20.95 | 100 | 13.68 | 6.47 | 7 |
| 4.45 | 19.83 | 20 | 14.36 | 6.16 | 10 |
| 4.98 | 17.72 | 54 | 14.98 | 5.91 | 13 |
| 5.69 | 15.52 | 8 | 15.51 | 5.71 | 14 |
| 6.32 | 13.97 | 34 | 15.70 | 5.64 | 12 |
| 6.48 | 13.63 | 35 | 16.21 | 5.46 | 8 |
| 7.12 | 12.41 | 12 | 17.09 | 5.18 | 10 |
| 7.49 | 11.80 | 11 | 17.48 | 5.07 | 9 |
| 8.08 | 10.93 | 4 | 18.10 | 4.90 | 9 |
| 8.49 | 10.41 | 6 | 19.18 | 4.62 | 11 |
| 8.96 | 9.86 | 7 | 19.43 | 4.56 | 13 |
| 9.50 | 9.31 | 5 | 19.95 | 4.45 | 11 |
| 10.19 | 8.68 | 5 | 20.89 | 4.25 | 11 |
| 10.80 | 8.18 | 8 | 21.29 | 4.17 | 10 |
| 11.16 | 7.92 | 18 | 22.19 | 4.00 | 9 |
| 11.88 | 7.44 | 7 | 23.07 | 3.85 | 10 |
| 12.51 | 7.07 | 7 | 23.76 | 3.74 | 9 |
| 12.79 | 6.92 | 11 | 24.43 | 3.64 | 8 |

In the above Table the value "2Θ[°]" denotes the angle of diffraction in degrees and the value "d [Å]" denotes the lattice plane spacings determined in Å.

According to the findings given in Table 1, the crystalline form of telmisartan sodium that constitutes the invention is characterised in that, when subjected to analysis by x-ray powder diffraction, it exhibits a characteristic set of d-spacings that includes values at d 20.95 Å, 17.72 Å, 13.97 Å and 13.63 Å.

The X-ray powder diagrams were recorded within the scope of the present invention using a Bruker D8 Advanced with an SSD (=site-sensitive detector) ($CuK_\alpha$—radiation, λ=1.5418 Å, 30 kV, 40 mA).

The present invention also comprises the solvates and hydrates of the above-described crystalline form of telmisartan sodium, especially the hydrates, most especially the hemihydrate thereof.

In another aspect, the present invention comprises a method of producing the crystalline form of telmisartan sodium according to the invention. The starting material used to prepare the crystalline telmisartan sodium according to the invention may be the free acid of telmisartan, which may be obtained by methods known in the art (e.g. according to EP 502314 A1 and U.S. Pat. No. 5,591,762).

To prepare the crystalline telmisartan sodium according to the invention the free acid of telmisartan is taken up in a suitable solvent, preferably in an organic aprotic solvent, most preferably in an organic, aprotic and non-polar solvent. The solvents used according to the invention are most preferably toluene, chloroform, dichloromethane, tetrahydrofuran, diethylether, diisopropylether, methyl-tert-butylether, acetone, methylisobutylketone, benzene or acetonitrile, of which toluene, benzene and methylisobutylketone are particularly preferred. Of outstanding importance according to the invention is toluene as solvent.

Preferably, between 0.5 and 5 ml, more preferably between 1 and 3 ml, most preferably between 1.5 and 2.5 ml of the abovementioned solvent are used per gram of telmisartan (free acid).

A suitable sodium salt is then added as a base to this solution or suspension. Suitable sodium salts within the scope of the present invention include sodium hydroxide, sodium hydride, sodium carbonate, sodium hydrogen carbonate or sodium alkoxides. By sodium alkoxides are meant the sodium salts which are formed with lower alcohols, preferably with alcohols selected from among methanol, ethanol, isopropanol, n-propanol, tert-butanol, sec.-butanol, isobutanol, n-butanol and tert.-amylalcohol. Of particular interest according to the invention are sodium salts selected from among sodium hydroxide, sodium hydride, sodium ethoxide and sodium methoxide; of these, sodium hydroxide and sodium methoxide are of particular importance according to the invention. The abovementioned sodium salts may be added to the reaction mixture as solids. In the case of sodium hydroxide this is preferably added in the form of aqueous solutions, however. It is particularly preferable to use concentrated aqueous solutions of sodium hydroxide.

For example, sodium hydroxide solution may be used in a concentration of about 45 wt.-%

The amount of sodium salt to be used naturally depends on the amount of free acid telmisartan used. According to the invention at least 1 mol of sodium salt has to be added per mol of telmisartan. It is also possible according to the invention to add an excess of sodium salt. Preferably, 1–2.5, more preferably 1–2, most preferably 1–1.5 mol of sodium salt are added per mol of the acid telmisartan used.

If sodium hydroxide is used as the sodium salt and this is added in the form of an aqueous solution, according to a preferred embodiment of the process according to the invention, it may be helpful in some cases to add a water-miscible organic solvent. This is preferably selected from among methanol, ethanol, isopropanol, acetone, tetrahydrofuran, tert.-butanol, 2-butanol, butanol, glycol, ethyldiglycol, 1,3-butanediol, 1,4-butanediol, tert.-amylalcohol, acetonitrile, nitromethane, formamide, dimethylformamide, N-methylpyrrolidinone, dimethylsulphoxide, dimethylacetamide, nitroethane and methoxy-2-propanol, of which the abovementioned alcohols are particularly significant. It is particularly preferred, within the scope of the process according to the invention, to use methanol or ethanol, most preferably ethanol. Preferably, between 50 and 500 ml, more preferably between 100 and 400 ml, most preferably between 200 and 350 ml of this solvent are used per mol of telmisartan used, according to the invention.

Then the reaction mixture may be heated to speed up the progress of the reaction. Preferably, the reaction mixture is heated to a temperature of >40° C., most preferably to over 60° C., with thorough mixing. The maximum temperature which may be selected is naturally determined by the boiling temperature of the solvents used. If the preferred solvents as described hereinbefore are used according to the invention, the mixture is preferably heated to over 70° C. This heating is generally carried out for a period of from 15 minutes to 2 hours, preferably between 20 minutes and one hour. Then the solution obtained is filtered and any solid remaining in the filter is washed with one or more of the abovementioned solvents.

The filtrate obtained by the process described above is added slowly, preferably dropwise, to an organic solvent which is heated to a temperature of >40° C., preferably above 60° C., most preferably to boiling point. The solvent used is preferably an organic aprotic solvent, more preferably an organic, aprotic and non-polar solvent. Solvents which may be used according to the invention are, most preferably, toluene, chloroform, dichloromethane, tetrahydrofuran, diethylether, diisopropylether, methyl-tert. butylether, acetone, methylisobutylketone, benzene or acetonitrile, of which toluene, benzene and methylisobutylketone are particularly preferred. The solvent toluene is of exceptional importance according to the invention. At the same time as the filtrate is added to the heated solvent, in a preferred embodiment of the invention, some of the solvent is distilled off (optionally azeotropically). After all the filtrate has been added, more solvent (e.g. about one to two thirds of the total amount of solvent added by this stage) may optionally be removed by distillation.

The concentrated solution thus obtained is cooled, preferably to ambient temperature, whereupon the telmisartan sodium salt crystallises out. After crystallisation is complete the crystals are separated off, optionally washed with the organic solvent mentioned above and finally dried.

In another embodiment of the invention the crystalline telmisartan sodium salt according to the invention may be obtained starting from the acid addition salts of formula 2

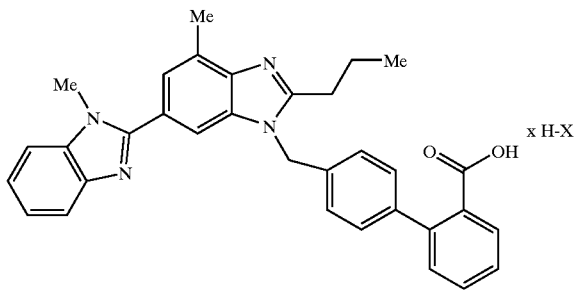

2 wherein H—X denotes an acid selected from among hydrochloric acid, hydrobromic acid, toluenesulphonic acid or methanesulphonic acid. Of the abovementioned acid addition salts of formula 2 the salt wherein H—X denotes hydrochloric acid is of particular significance. This acid addition salts is also referred to hereinafter as telmisartan hydrochloride.

The compounds of formula 2 may be obtained for example from tert.-butyl 4'-[[2-n-propyl-4-methyl-6-(1-methylbenzimidazol-2-yl)-benzimidazol-1-yl]-methyl]-biphenyl-2-carboxylate (=tert.-butyl ester of telmisartan) known from the prior art by saponification in acetic acid in the presence of the acid H—X.

In order to prepare the crystalline telmisartan sodium salt of formula I according to the invention starting from the acid addition salts of formula 2 the following procedure may be used, according to the invention.

The compound of formula 2 is taken up in a suitable solvent and combined with a suitable sodium salt.

The solvent may be water and/or a suitable alcohol, such as methanol, ethanol or isopropanol mixed with an aprotic organic solvent selected from among toluene, chloroform, dichloromethane, tetrahydrofuran, diethylether, diisopropylether, methyl-tert. butylether, acetone, methylisobutylketone, benzene and acetonitrile. It is particularly preferred to use, as the solvent, water mixed with ethanol or isopropanol mixed with an aprotic organic solvent selected from among toluene, benzene and methylisobutylketone, most preferably toluene. A mixture of water, isopropanol and toluene has proved particularly suitable for this step of the synthesis.

The amount of solvent or solvent mixture used depends on the amount of acid addition salt 2 used. Preferably, about 0.3–3.5 L, preferably about 1–2.5 L, more preferably about 1.5–2 L of the abovementioned solvent or solvent mixture are used per mol of compound 2 used. If the solvent used is the preferred solvent mixture according to the invention which contains an alcohol as the third solvent component in addition to water and an aprotic organic solvent, the ratios by volume of water to aprotic organic solvent according to the invention are preferably in a range from 1:5 to 1:50 and the ratio of water to alcohol used is in a range from 2:1 to 1:40. Preferably, in a solvent mixture of this kind, the ratios of water to aprotic organic solvent are in the range from 1:10 to 1:30, preferably in the range from 1:15 to 1:25 and the ratio of water to alcohol used is in a range from 1:1 to 1:20, preferably in the range from 1:5 to 1:15.

Preferably, the solvent or solvent mixture mentioned above contains about 10 to 100 ml of water, preferably about 30 to 80 ml of water, most preferably about 40 to 70 ml of water, per mol of 2. Preferably the solvent or solvent mixture used also contains about 100 to 1000 ml of alcohol, preferably about 300 to 800 ml alcohol, most preferably about 400 to 700 ml alcohol, per mol of 2. Finally, the solvent or solvent mixture used preferably contains as the third component of the solvent, about 200 to 2000 ml of the abovementioned aprotic organic solvent, preferably about 600 to 1600 ml, most preferably about 800 to 1400 ml of the abovementioned aprotic organic solvent, per mol of 2.

Suitable sodium salts which may be used for reacting 2 to 1 include sodium hydroxide, sodium hydride, sodium carbonate, sodium hydrogen carbonate or sodium alkoxides. By sodium alkoxides are meant the sodium salts which are formed with lower alcohols, preferably with alcohols selected from among methanol, ethanol, isopropanol, n-propanol, tert-butanol, sec.-butanol, isobutanol, n-butanol and tert.-amylalcohol. Of particular interest according to the invention are sodium salts selected from among sodium hydroxide, sodium hydride, sodium ethoxide and sodium methoxide, while the sodium alkoxides sodium ethoxide and sodium methoxide, particularly sodium methoxide are of particular importance according to the invention for this reaction step. The abovementioned sodium salts may be added to the reaction mixture as solids. In the case of sodium methoxide however it is preferable to add it in the form of a methanolic solution. Methanolic solutions of sodium methoxide which contain it in a concentration of at least 10%, most preferably about 20–40% (w/w), are particularly preferred. For example, the methanolic sodium methoxide solution used may have a concentration of about 30 wt. %.

The amount of sodium salt to be used is naturally dependent on the amount of free acid telmisartan used. According to the invention, at least 2 mol of sodium salt have to be added per mol of telmisartan acid addition salt of formula 2 used. According to the invention it is also possible to add an excess of sodium salt. It may be useful in some cases to add activated charcoal to the abovementioned reaction mixture. For example, it may be added in an amount of about 5–50 g per mol of 2 used, preferably in an amount of about 10–40 g per mol of 2 used. After the sodium salt and optionally the activated charcoal has been added the reaction mixture obtained is heated to a temperature of about 50–100° C., preferably about 60–90° C., most preferably about 70–80° C. for a period of about 10 minutes to 2 hours, preferably for about 20–45 minutes. In the course of this heating, some of the solvent, preferably about 10–50%, most preferably about 20–40% of the total quantity of solvent may be distilled off. The remaining suspension is then filtered, the filter residue is optionally washed with one of the abovementioned aprotic organic solvents, preferably with the aprotic organic solvent which is also used in the reaction. The filtrate obtained is then diluted with a solvent or mixture of solvents. It is preferable to use a mixture of water and the abovementioned aprotic organic solvent for this. Preferably, at this point, about 10 to 100 ml of water, preferably about 30 to 80 ml of water, most preferably about 40 to 70 ml of water are used per mol of the compound 2 originally used. At this point, 250 to 3000 ml, preferably about 800 to 2000 ml, most preferably about 1200 to 1800 ml of aprotic organic solvent are used per mole of the compound 2 originally used. After dilution, the mixture obtained is refluxed. Then about 1–2 L, preferably about 1200 to 1800 ml of solvent are distilled off per mole of the compound 2 originally used. After the solvent has been distilled off the telmisartan-sodium salt 1 according to the invention crystallises out. The crystals obtained are isolated, optionally washed with one of the abovementioned aprotic organic solvents and then dried.

In another aspect the present invention relates to crystalline telmisartan-sodium salt, optionally in the form of the solvates or hydrates thereof, preferably in the form of the hydrates thereof, most preferably in the form of the hemihydrate, which may be obtained by the methods described above.

Because of the central significance of the compounds of formula 2 as valuable starting materials for the direct synthesis of the telmisartan-sodium salt 1 according to the invention, in another aspect the present invention relates to compounds of formula 2 per se

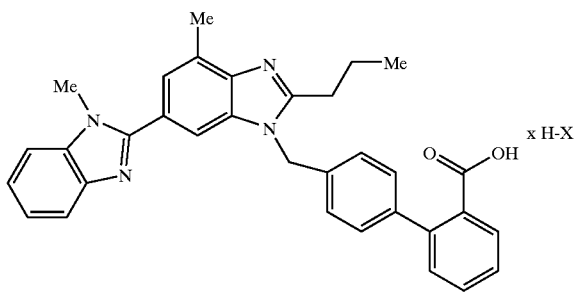

2 wherein H—X denotes an acid selected from among hydrochloric acid, hydrobromic acid, toluenesulphonic acid or methanesulphonic acid. The compound of formula 2 wherein H—X denotes hydrogen chloride, the telmisartan hydrochloride, is particularly preferred.

Most preferably, the present invention further relates to the abovementioned compounds of formula 2 in crystalline form.

Moreover, in view of the pharmaceutical activity of the crystalline telmisartan sodium salt according to the invention, the present invention relates to the use thereof as a pharmaceutical composition.

In another aspect, in view of the pharmaceutical activity of the crystalline telmisartan sodium salt according to the invention, the present invention relates to the use thereof for preparing a pharmaceutical composition, particularly for preparing a pharmaceutical composition for the prevention or treatment of diseases wherein the administration of therapeutically effective doses of one or more angiotensin-II-antagonists may provide a therapeutic benefit. Preferably, the present invention relates to the use of crystalline telmisartan-sodium salt for preparing a pharmaceutical composition for the prevention or treatment of diseases selected from among hypertension, cardiac insufficiency, ischaemic peripheral circulatory disorders, myocardial ischaemia (angina), the progression of cardiac insufficiency after myocardial infarct, diabetic neuropathy, glaucoma, gastrointestinal diseases and bladder diseases, the prevention or treatment of hypertension being particularly preferred.

Accordingly, in another aspect, the present invention is directed to pharmaceutical formulations characterised in that they contain crystalline telmisartan-sodium salt.

The example of synthesis that follows serves to illustrate a method of preparing crystalline telmisartan-sodium salt carried out by way of example. It is intended solely as a possible procedure provided by way of example, without restricting the invention to its contents.

SYNTHESIS EXAMPLE 1

Preparation of Crystalline Telmisartan-Sodium Salt Starting from Telmisartan

The starting material used to prepare crystalline telmisartan-sodium salt according to the invention may be the free acid, which may be obtained by methods known from the prior art (e.g. according to EP 502314 A1).

154.4 g of telmisartan are placed in 308.8 ml of toluene in a suitable reaction vessel. The suspension is combined with 27.8 g of 44.68% sodium hydroxide solution and 84.9 ml of ethanol and heated to 78° C. for about 30 min, then the mixture is filtered. If desired, if large amounts of solid are left in the filter, this may be washed with a mixture of 61.8 ml of toluene and 15.3 ml of ethanol.

463.2 ml of toluene are placed in another reaction vessel and refluxed. The filtrate obtained by the process described above is slowly added thereto at boiling temperature and simultaneously distilled off azeotropically. After it has all been added the solution which may have been obtained from washing the filter is also added and again distilled off azeotropically. The mixture is distilled at up to 103° C. and the suspension is allowed to cool to ambient temperature. The crystals are suction filtered, washed with 154.4 ml of toluene and dried at 60° C. in the circulating air drier.

Yield: 154.6 g (96%) of colourless crystals;

| $C_{33}H_{29}N_4O_2Na \times 0.5\ H_2O$ | calc.: | C 72.51 | H 5.72 | N 10.25 |
|---|---|---|---|---|
| | found: | C 72.57 | H 5.69 | N 10.21 |

SYNTHESIS EXAMPLE 2

Preparation of Crystalline Telmisartan-Sodium Salt Starting from Telmisartan Hydrochloride A) Preparation of Telmisartan-Hydrochloride:

411 g of tert.-butyl 4'-[[2-n-propyl-4-methyl-6-(1-methylbenzimidazol-2-yl)-benzimidazol-1-yl]-methyl]-biphenyl-2-carboxylate are suspended in 822 ml of glacial acetic acid and combined with 213 g of concentrated aqueous hydrochloric acid (37%). The mixture is refluxed and about 640 ml of solvent are distilled off. The residue remaining is slowly combined with about 620 ml of water at 50–60° C. To this mixture are added 20 g of activated charcoal (e.g. Norit SX 2 Ultra) and the resulting mixture is stirred for about 10 min at constant temperature. After filtering, the residue is washed three times with 25 ml of glacial acetic acid and about 620 ml of water. The filtrate obtained is again heated to about 50–60° C. and about 2 L of water are added. After stirring for about 12 hours at about 23° C. the crystals formed are suction filtered and washed twice with about 500 ml of water, once with about 900 ml of acetone and then dried at about 60° C.

Yield: 367 g (92.5%), colourless crystals, melting point: =278° C.

B) Preparation of Crystalline Telmisartan Sodium Salt from Telmisartan Hydrochloride 55.1 g of telmisartan hydrochloride are taken up in 110.2 ml of toluene, 5.5 ml of water, 55.1 ml of isopropanol and this mixture is combined with 36.9 g of sodium methoxide (30% in methanol) and 2.75 g of activated charcoal (e.g. Sorit SX 2 Ultra). The mixture is then heated to about 75° C., and about 50 ml of solvent mixture are distilled off at constant temperature over about 30 min. The suspension obtained is filtered and the residue is washed with about 20 ml of toluene. The filtrate is combined with about 5 ml of water and about 150 ml of toluene. The mixture obtained is refluxed. During this time about 150 ml of solvent mixture are azeotropically distilled off (at up to 102° C.). The mixture is left to crystallise for one hour at 100° C. The crystals are suction filtered, washed with about 50 ml of toluene and dried at about 60° C.

Yield: 53.6 g (99%), colourless crystals;

| $C_{33}H_{29}N_4O_2Na \cdot 0.5\ H_2O$ | calc.: | C 72.51 | H 5.72 | N 10.25 |
|---|---|---|---|---|
| | found: | C 72.44 | H 5.68 | N 10.20 |

To prepare a pharmaceutical composition containing the active substance, particularly an orally administered pharmaceutical composition, most preferably a tablet, procedures known in the art may be used.

Suitable tablets may be obtained, for example, by mixing the active substance(s) with known excipients, for example inert diluents such as calcium carbonate, calcium phosphate or lactose, disintegrants such as maize starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

The following are some examples of pharmaceutical preparations which may be used according to the invention. They are intended purely as illustrations by way of example without restricting the subject matter of the invention thereto.

| TABLET 1: | |
|---|---|
| Ingredients: | mg |
| Telmisartan-sodium salt hemihydrate | 1.00 |
| Mannitol | 121.50 |
| Maize starch | 79.85 |
| Highly dispersed silicon dioxide, anhydrous | 2.30 |
| Polyvidon K25 | 2.35 |
| Magnesium stearate | 3.00 |
| Total | 210.00 |

| TABLET 2: | |
|---|---|
| Ingredients: | mg |
| Telmisartan-sodium salt hemihydrate | 0.5 |
| Mannitol | 122.0 |
| Maize starch. dried | 61.8 |
| Maize starch | 18.0 |
| Highly dispersed silicon dioxide, anhydrous | 2.4 |
| Polyvidon K25 | 2.3 |
| Magnesium stearate | 3.0 |
| Total | 210.0 |

| TABLET 3: | |
|---|---|
| Ingredients: | mg |
| Telmisartan-sodium salt hemihydrate | 0.25 |
| Mannitol | 61.00 |
| Maize starch | 39.90 |
| Highly dispersed silicon dioxide, anhydrous | 1.20 |
| Polyvidon K25 | 1.15 |
| Magnesium stearate | 1.5 |
| Total | 105.00 |

What is claimed is:

1. The crystalline form of telmisartan sodium which has a melting point of T=245±5° C.

2. The crystalline form of telmisartan sodium according to claim 1, which, when subjected to analysis by X-ray powder diffraction, exhibits a characteristic set of d-spacings that includes values at d=20.95 Å, 17.72 Å, 13.97 Å and 13.63 Å.

3. A solvate or hydrate of the crystalline form of telmisartan sodium according to claim 2.

4. A hydrate of the crystalline telmisartan-sodium salt according to claim 2.

5. A process for preparing crystalline telmisartan sodium, comprising the following steps:

(a) dissolving the free acid of telmisartan in a suitable solvent, to produce a solution of telmisartan;

(b) combining the solution of telmisartan with a suitable sodium salt, using at least 1 mol of sodium salt per mol of telmisartan;

(c) heating the mixture produced in the preceding step for a period of from 15 minutes to 2 hours, to produce a solution of telmisartan sodium;

(d) filtering the solution telmisartan sodium obtained in the preceding step;

(e) adding the filtered solution of telmisartan sodium produced in the preceding step to an organic solvent that is heated to above 40° C.;

(f) cooling the solution of telmisartan sodium produced in the preceding step until the telmisartan sodium crystallizes, leaving crytalline telmisartan sodium and supernatant; and (g) separating the crystalline telmisartan sodium obtained in the previous step from the supernatant.

6. A process for preparing crystalline telmisartan sodium, wherein an acid addition salt of formula 2

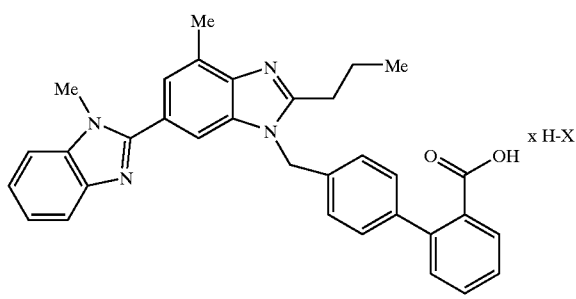

wherein H—X denotes an acid selected from the group consisting of hydrochloric acid, hydrobromic acid, toluenesulphonic acid and methanesulphonic acid, is taken up in a suitable solvent and reacted with a suitable sodium salt, using at least 2 mol of sodium salt per mol of the compound 2 used.

7. Crystalline telmisartan sodium obtained by the process of claim 5 or 6.

8. A pharmaceutical composition comprising crystalline telmisartan sodium in accordance with claim 1, 2, 3, 4 or 7, and a pharmaceutically acceptable carrier.

9. A pharmaceutical composition comprising crystalline telmisartan sodium in accordance with claim 7, and a pharmaceutically acceptable carrier.

* * * * *